United States Patent [19]

Aoki

[11] Patent Number: 4,996,209

[45] Date of Patent: Feb. 26, 1991

[54] OPHTHALMIC ANTIINFLAMMATORY COMPOSITIONS COMPRISING S(+)-FLURBIPROFEN

[75] Inventor: K. Roger Aoki, Fort Worth, Tex.

[73] Assignee: Alcon Laboratories, Inc., Fort Worth, Tex.

[21] Appl. No.: 532,482

[22] Filed: Jun. 4, 1990

Related U.S. Application Data

[63] Continuation of Ser. No. 208,449, Jun. 20, 1988, abandoned.

[51] Int. Cl.⁵ .................... A01N 43/90; A01N 43/42; A61K 31/52; A61K 31/44
[52] U.S. Cl. .................................... 514/263; 514/264; 514/300; 514/569; 514/570; 514/914
[58] Field of Search ............... 514/264, 914, 974, 300, 514/569, 570, 263; 424/253

[56] References Cited

U.S. PATENT DOCUMENTS 4,559,343  12/1985  Han et al. ............................ 514/264

Primary Examiner—Nathan M. Nutter
Attorney, Agent, or Firm—James A. Arno; Sally Yeager

[57] ABSTRACT

Disclosed are ophthalmic pharmaceutical compositions comprising S(+)-flurbiprofen substantially free of R(−)-flurbiprofen and methods of topical administration to the eye when indicated for treatment of inflammation.

3 Claims, No Drawings

OPHTHALMIC ANTIINFLAMMATORY COMPOSITIONS COMPRISING S(+)-FLURBIPROFEN

This is a continuation of U.S. patent application Ser. No. 208,449 filed on Jun. 20, 1988 now abandoned.

BACKGROUND OF THE INVENTION

This invention relates to the use of S(+)-flurbiprofen, substantially free of its enantiomorph, R(−)-flurbiprofen, as a topical ophthalmic antiinflammatory agent; and to pharmaceutical compositions comprising S(+)-flurbiprofen substantially free of R(−)-flurbiprofen.

U.S. Pat. No. 4,559,343, issued Dec. 12, 1985, discloses pharmaceutical compositions and methods of treatment employing various known, nonsteroidal analgesic/antiinflammatory agents, including racemic flurbiprofen. To the extent that this patent teaches the ophthalmic pharmacology of racemic flurbiprofen, it is incorporated herein by reference since such disclosure can be applied with efficiency in teaching the pharmaceutical compositions and methods of treatment employing S(+)-flurbiprofen of the present invention. However, as is disclosed in U.S. Pat. No. 4,559,343, flurbiprofen per se at appropriate dosage concentrations for ophthalmic delivery is generally perceived as stinging. Thus, it was the purpose of the disclosure in U.S. Pat. No. 4,559,343 to define formulations which tend to decrease the stinging sensation associated with the application of racemic flurbiprofen to the eye. The pharmaceutical compositions and methods of treatment of U.S. Pat. No. 4,559,343 employ a complex of flurbiprofen and a xanthine derivative, such as, caffeine to achieve the stated objective. The consensus of the clinical experience involving the disclosed xanthine-flurbiprofen compositions of U.S. Pat. No. 4,559,343, however, is that the alleged comfort formulation is only moderately improved. And this is particularly true in situations wherein the exquisitely sensitive cornea is rendered even more sensitive through compromised health or trauma.

With respect to the present invention, it is believed that substantially all of the ophthalmic antiinflammatory activity of racemic flurbiprofen resides in its S(+) enantiomorph. Further, ophthalmic formulations comprising S(+)-flurbiprofen substantially free of R(−)-flurbiprofen and at a concentration level of approximately one-half of the prior recommendations for the racemic mixture are believed to be equivalent in efficacy to prior art formulations containing the racemic mixture at twice that concentration; and it is further believed that such formulations may be employed at this one-half strength level without the acute stinging sensation which attends the use of full strength formulations of racemic flurbiprofen.

The expression, relative to the purity of S(+)-flurbiprofen, that it be "substantially free of R(−)-flurbiprofen" means that the R(−)-flurbiprofen enantiomorph is present in such mixtures at a concentration level of from 0 to 5%. Preparations of such substantially pure forms of S(+)-flurbiprofen can be achieved by known stereo-selective synthesis, or S(+)-flurbiprofen can be isolated from the racemic mixture by known conventional methods, such as, forming diastereoisomeric salts with optically active organic amines.

DETAILED DESCRIPTION OF THE INVENTION

Consistent with the teachings of the incorporated by reference U.S. Pat. No. 4,559,343, the ophthalmic antiinflammatory active disclosed as S(+)-flurbiprofen can be used with the xanthine derivatives. A representative formulation exemplifying the xanthine of choice, caffeine, is given below. In the alternative, pharmaceutical compositions comprising S(+)-flurbiprofen in aqueous solution, optionally containing a preservative for multidose use and other conventionally employed ophthalmic adjuvants, including a salt entity to adjust the tonicity of solutions, can be employed. The most preferred form of delivery is by eye drops; however, formulations wherein the final dosage form is a gel or ointment can also be employed and formulated according to conventional technology.

The S(+)-flurbiprofen component may be incorporated in the ophthalmic compositions of the present invention in accordance with known practices in order to provide an effective rate of delivery of the therapeutic agent to the eye when applied topically. The ophthalmic compositions will preferably contain between about 0.01 percent and about 1.5 percent by weight/volume of S(+)-flurbiprofen.

The compositions may contain preservatives such as thimerosal, chlorobutanol, benzalkonium chloride, Onamer M, or chlorhexidine; buffering agents, such as phosphates, borates, carbonates and citrates; and thicknening agents, such as, high molecular weight carboxy vinyl polymers, including those sold under the name of CARBOPOL which are available from the B.F. Goodrich Chemical Company, hydroxymethylcellulose, or polyvinyl alcohol.

The compositions are prepared by dissolving the various ingredients in the required amount of water with stirring to ensure that all the ingredients are dissolved. The aqueous compositions of the invention may be solutions, suspensions, or gels. After preparation of the solution, suspension, or gel the compositions are then packaged in dispensers suitable for delivery of the ophthalmic composition.

The following examples of ophthalmic compositions typify the manner in which the invention may be practiced. The examples should be construed as illustrative, and not as a limitation upon the overall scope of the invention. The percentages are expressed on a relative mass basis.

EXAMPLE I

| Ingredient | Amount |
|---|---|
| S(+)-flurbiprofen | 0.3% |
| PLURONIC F127* | 0.5% |
| Benzalkonium Chloride | 0.01% + 10% excess |
| Disodium Edetate | 0.1% |
| Dried Sodium Phosphate | 0.1% |
| Sodium Biphosphate | 0.03% |
| Sodium Chloride | 0.6% |
| pH adjustment with NaOH or HCl | q.s. pH 7.4 |
| Purified Water | q.s. 100% |

*a high molecular weight non-ionic surfactant sold under the registered trademark of the Wyandotte Chemical Corporation.

EXAMPLE II

| Ingredient | Amount |
|---|---|
| S(+)-flurbiprofen | 0.3% |

EXAMPLE II -continued

| Ingredient | Amount |
| --- | --- |
| Caffeine | 1.0% |
| PLURONIC F127 | 0.5% |
| Benzalkonium Chloride | 0.01% + 10% excess |
| Disodium Edetate | 0.1% |
| Dried Sodium Phosphate | 0.1% |
| Sodium Biphosphate | 0.03% |
| Sodium Chloride | 0.6% |
| pH adjustment with NaOH or HCl | q.s. pH 7.4 |
| Purified Water | q.s. 100% |

What is claimed is:

1. An ophthalmic, antiinflammatory composition for topical application to the eye consisting essentially of a therapeutically effective amount of S(+)-flurbiprofen substantially free of R(−)-flurbiprofen, and a pharmaceutically acceptable vehicle therefor.

2. An ophthalmic composition according to claim 1, wherein said S(+)-flurbiprofen comprises between about 0.01 to about 1.5 percent by weight/volume of said ophthalmic composition.

3. A method of treating ophthalmic inflammation which comprises applying a therapeutically effective amount of a composition according to claim 1 topically to the affected eye.

* * * * *